United States Patent
Gonzalez et al.

(10) Patent No.: US 11,860,154 B2
(45) Date of Patent: Jan. 2, 2024

(54) METHOD TO DETECT WHITE BLOOD CELLS AND/OR WHITE BLOOD CELL SUBTYPES FROM NON-INVASIVE CAPILLARY VIDEOS

(71) Applicant: Leuko Labs, Inc., Boston, MA (US)

(72) Inventors: Carlos Castro Gonzalez, Cambridge, MA (US); Ian Butterworth, Somerville, MA (US); Aurelien Bourquard, Madrid (ES); Alvaro Sanchez Ferro, Madrid (ES)

(73) Assignee: Leuko Labs, Inc, Boston, MA (US)

( * ) Notice: Subject to any disclaimer, the term of this patent is extended or adjusted under 35 U.S.C. 154(b) by 405 days.

(21) Appl. No.: 17/331,893

(22) Filed: May 27, 2021

(65) Prior Publication Data

US 2021/0374963 A1 Dec. 2, 2021

Related U.S. Application Data

(60) Provisional application No. 63/031,117, filed on May 28, 2020.

(51) Int. Cl.
  *G01N 33/49* (2006.01)
  *G06T 7/00* (2017.01)
  (Continued)

(52) U.S. Cl.
  CPC ........... *G01N 33/49* (2013.01); *G01N 15/147* (2013.01); *G01N 15/1429* (2013.01);
  (Continued)

(58) Field of Classification Search
  None
  See application file for complete search history.

(56) References Cited

U.S. PATENT DOCUMENTS

| 534,211 A | 2/1895 | English |
|---|---|---|
| 2,588,528 A | 3/1952 | Howser |

(Continued)

FOREIGN PATENT DOCUMENTS

| CN | 1108082 A | 9/1995 |
|---|---|---|
| CN | 1342054 A | 3/2002 |

(Continued)

OTHER PUBLICATIONS

WIPO International Preliminary Report on Patentability Chapter 1, Sep. 21, 2021, PCT/US2021/034455 (Year: 2021).*

(Continued)

*Primary Examiner* — Emily C Terrell
*Assistant Examiner* — Nathan J Bloom
(74) *Attorney, Agent, or Firm* — Iandiorio Teska & Coleman, LLP

(57) ABSTRACT

In one aspect, a method to detect white blood cells and/or white blood cell subtypes from non-invasive capillary videos is featured. The method includes acquiring a first plurality of images of a region of interest including one or more capillaries of a predetermined area of a human subject from non-invasive capillary videos captured with an optical device, processing the first plurality of images to determine one or more optical absorption gaps located in said capillary, and annotating the first plurality of images with an indication of any optical absorption gap detected in the first plurality of images. The method also includes acquiring a second plurality of images of the same region of interest of the same capillary with an advanced optical device capable of resolving cellular structure of white blood cells and white blood cell subtypes and spatiotemporally annotating the second plurality of images with an indication of any white blood cell detected and/or a subtype of any white blood cell detected in the second plurality of images. The method also (Continued)

includes inputting the first plurality of images and annotated information from the first plurality of images and annotated information from the spatiotemporally annotated second plurality of images into a machine learning subsystem configured to determine a presence of white blood cells and/or the subtype of any white blood cells present in the one or more optical absorption gaps in the first plurality of images.

24 Claims, 11 Drawing Sheets

(51) Int. Cl.
| | |
|---|---|
| *G06T 7/11* | (2017.01) |
| *G06T 7/38* | (2017.01) |
| *G16H 30/20* | (2018.01) |
| *G16H 30/40* | (2018.01) |
| *G16H 50/20* | (2018.01) |
| *G16H 50/70* | (2018.01) |
| *G01N 21/31* | (2006.01) |
| *G06V 20/69* | (2022.01) |
| *G06F 18/214* | (2023.01) |
| *G06V 10/764* | (2022.01) |
| *G06V 10/82* | (2022.01) |
| *G06V 10/56* | (2022.01) |
| *G01N 15/14* | (2006.01) |
| *G01N 15/00* | (2006.01) |
| *G01N 15/10* | (2006.01) |

(52) U.S. Cl.
CPC ......... *G01N 15/1475* (2013.01); *G01N 21/31* (2013.01); *G06F 18/2148* (2023.01); *G06T 7/0016* (2013.01); *G06T 7/11* (2017.01); *G06T 7/38* (2017.01); *G06V 10/56* (2022.01); *G06V 10/764* (2022.01); *G06V 10/82* (2022.01); *G06V 20/695* (2022.01); *G06V 20/698* (2022.01); *G16H 30/20* (2018.01); *G16H 30/40* (2018.01); *G16H 50/20* (2018.01); *G16H 50/70* (2018.01); *G01N 2015/008* (2013.01); *G01N 2015/0073* (2013.01); *G01N 2015/1006* (2013.01); *G01N 2015/1443* (2013.01); *G01N 2015/1486* (2013.01); *G06T 2207/10016* (2013.01); *G06T 2207/10056* (2013.01); *G06T 2207/20081* (2013.01); *G06T 2207/20084* (2013.01); *G06T 2207/30101* (2013.01); *G06T 2207/30242* (2013.01); *G06V 2201/03* (2022.01)

(56) References Cited

U.S. PATENT DOCUMENTS

| | | | |
|---|---|---|---|
| 4,998,533 | A | 3/1991 | Winkelman |
| 5,068,536 | A | 11/1991 | Rosenthal |
| 5,077,476 | A | 12/1991 | Rosenthal |
| 5,086,229 | A | 2/1992 | Rosenthal et al. |
| 5,204,532 | A | 4/1993 | Rosenthal |
| 5,218,207 | A | 6/1993 | Rosenthal |
| 5,237,178 | A | 8/1993 | Rosenthal et al. |
| 5,362,966 | A | 11/1994 | Rosenthal et al. |
| 5,365,066 | A | 11/1994 | Krueger, Jr. et al. |
| 5,436,455 | A | 7/1995 | Rosenthal et al. |
| 5,452,717 | A | 9/1995 | Branigan et al. |
| 5,582,705 | A | 12/1996 | Yeung et al. |
| 5,596,987 | A | 1/1997 | Chance |
| 5,598,842 | A | 2/1997 | Ishihara et al. |
| 5,676,143 | A | 10/1997 | Simonsen et al. |
| 5,782,757 | A | 7/1998 | Diab et al. |
| 5,926,261 | A | 7/1999 | Hoshino |
| 5,934,278 | A | 8/1999 | Ishihara et al. |
| 5,983,120 | A | 11/1999 | Groner et al. |
| 6,041,247 | A | 3/2000 | Weckstrom et al. |
| 6,213,952 | B1 | 4/2001 | Finarov et al. |
| 6,246,786 | B1 | 6/2001 | Nishikiori et al. |
| 6,358,208 | B1 | 3/2002 | Lang et al. |
| 6,424,851 | B1 | 7/2002 | Berman et al. |
| 9,556,416 | B2 | 1/2017 | Luscher et al. |
| 9,984,277 | B2 | 5/2018 | Castro-Gonzalez et al. |
| 11,244,452 | B2 | 2/2022 | Castro-Gonzalez et al. |
| 2001/0002431 | A1 | 5/2001 | Gurley |
| 2005/0209514 | A1 | 9/2005 | Oshima et al. |
| 2005/0268369 | A1 | 12/2005 | Santiago |
| 2006/0060770 | A1 | 3/2006 | Page et al. |
| 2006/0161063 | A1 | 7/2006 | Shau |
| 2007/0092115 | A1 | 4/2007 | Usher et al. |
| 2007/0116345 | A1 | 5/2007 | Peterson et al. |
| 2007/0161877 | A1 | 7/2007 | Arai et al. |
| 2007/0260129 | A1 | 11/2007 | Chin |
| 2008/0079723 | A1 | 4/2008 | Hanson et al. |
| 2009/0005693 | A1 | 1/2009 | Brauner et al. |
| 2009/0018417 | A1 | 1/2009 | Wang |
| 2009/0093970 | A1 | 4/2009 | Lewy et al. |
| 2010/0104169 | A1 | 4/2010 | Yamada |
| 2010/0254582 | A1 | 10/2010 | Liu et al. |
| 2010/0292629 | A1 | 11/2010 | Dacey, Jr. et al. |
| 2011/0134426 | A1 | 6/2011 | Kaduchak et al. |
| 2011/0275908 | A1 | 11/2011 | Baumann |
| 2012/0269420 | A1 | 10/2012 | Najarian et al. |
| 2013/0011055 | A1 | 1/2013 | You et al. |
| 2013/0235949 | A1 | 9/2013 | Jeckeln |
| 2014/0038206 | A1 | 2/2014 | Holmes et al. |
| 2014/0085482 | A1 | 3/2014 | Teich et al. |
| 2014/0092377 | A1 | 4/2014 | Liu et al. |
| 2014/0160481 | A1 | 6/2014 | Ahner et al. |
| 2014/0232869 | A1 | 8/2014 | May et al. |
| 2014/0240667 | A1 | 8/2014 | Uji et al. |
| 2014/0249784 | A1 | 9/2014 | Sankaran et al. |
| 2014/0273076 | A1 | 9/2014 | Adams et al. |
| 2015/0169641 | A1 | 6/2015 | Alldrin et al. |
| 2016/0148038 | A1 | 5/2016 | Castro-Gonzalez et al. |
| 2017/0138849 | A1* | 5/2017 | Tucker-Schwartz ........................ G01N 15/1429 |
| 2019/0139221 | A1 | 5/2019 | Castro-Gonzalez et al. |
| 2019/0228527 | A1* | 7/2019 | Ramirez ................ G16B 50/30 |
| 2020/0116698 | A1 | 4/2020 | Zelmanovic et al. |
| 2020/0237272 | A1* | 7/2020 | Lin ........................ G02B 21/14 |
| 2021/0022665 | A1 | 1/2021 | Butterworth |
| 2022/0113256 | A1* | 4/2022 | Verma ...................... C12Q 1/04 |
| 2022/0254024 | A1* | 8/2022 | Castro-Gonzalez ........................ A61B 5/7267 |
| 2023/0032932 | A1* | 2/2023 | Butterworth ....... G02B 19/0085 |

FOREIGN PATENT DOCUMENTS

| | | |
|---|---|---|
| CN | 1399131 A | 2/2003 |
| EP | 0641542 A2 | 3/1995 |
| KR | 101273692 B1 | 6/2013 |
| WO | 0122741 A2 | 3/2001 |
| WO | 0207276 A1 | 1/2002 |
| WO | 2013173446 A1 | 11/2013 |
| WO | 2017127732 A1 | 7/2017 |

OTHER PUBLICATIONS

Mudugamuwa, A. P., S. P. Hettiarachchi, and B. A. D. J. C. K. Basnayake. "Review on Photomicrography Based Full Blood Count (FBC) Testing and Recent Advancements." (Dec. 4, 2021). (Year: 2021).*

Fei Ye, Songchao Yin, Meirong Li, Yujie Li, Jingang Zhong, "In-vivo full-field measurement of microcirculatory blood flow velocity based on intelligent object identification," J. Biomed. Opt. 25(1), 016003 (Jan. 22, 2020), doi: 10.1117/1.JBO.25.1.016003 (Year: 2020).*

Nitkunanantharajah S et al L. Three-dimensional optoacoustic imaging of nailfold capillaries in systemic sclerosis and its potential for

(56) References Cited

OTHER PUBLICATIONS disease differentiation using deep learning. Scientific reports. Oct. 5, 2020;10(1):16444. (Year: 2020).*
Chen CL, Mahjoubfar A, Tai LC, Blaby IK, Huang A, Niazi KR, Jalali B. Deep learning in label-free cell classification. Scientific reports. Mar. 15, 2016;6(1):21471. (Year: 2016).*
Eden E, Waisman D, Rudzsky M, Bitterman H, Brod V, Rivlin E. An automated method for analysis of flow characteristics of circulating particles from in vivo video microscopy. IEEE Transactions on Medical Imaging. Aug. 1, 2005;24(8):1011-24. (Year: 2005).*
Doshi et al., "Computer-Aided Analysis of Nailfold Capillaroscopy Images", Handbook of Research on Trends in the Diagnosis and Treatment of chronic Conditions, Chapter 7, IGI Global, 2016, pp. 146-158.
Extended European Search Report in European Patent Application No. 15862463.5, dated Sep. 11, 2018, 7 pages.
Grassi et al., "Capillaroscopy: Questions and Answers", Clinical Rheumatology, Review Article, published Jul. 14, 2007, pp. 2009-2216.
Allen et al., "Computer Based System For Acquisition and Analysis of Nailfold Capillary Images," Medical Image Understanding & Analysis, (2003): 1-4.
Anderson et al., "Computerized Nailfold Video Capillaroscopy—A New Tool for Assessment of Raynaud's Phenomenon," J. Rheumatology 32.5 (2005): 841-848.
Bourquard et al., "Non-Invasive Detection of Severe Neutropenia in Chemotherapy Patients by Optical Imaging of Nailfold Microcirculation." Scientific Reports 8.1 (2018): 1-12.
Bourquard, Aurélien, et al. "Analysis of White Blood Cell Dynamics in Nailfold Capillaries." 2015 37th Annual International Conference of the IEEE Engineering in Medicine and Biology Society (EMBC). IEEE, 2015, 11 pages.
Brown et al., "Rigidity of Circulating Lymphocytes is Primarily Conferred by Vimentin Intermediate Filaments", The Journal of Immunology, 166.11 (2001): 6640-6646.
Delgado-Gonzalo et al., "Spline-Based Framework for Interactive Segmentation in Biomedical Imaging," IRBM 34.3 (2013): 235-243.
Drew, Patrick J., et al. "Rapid Determination of Particle Velocity from Space-Time Images Using the Radon Transform." Journal of Computational Neuroscience 29.1-2 (2009): 5-11.
Eden et al., "An Automated Method for Analysis of Flow Characteristics of Circulating Particles from In Vivo Video Microscopy," IEEE Transactions on Medical Imaging 24.8 (2005): 1011-1024.
Etehad Tavakol, Mahnaz, et al. "Nailfold Capillaroscopy in Rheumatic Diseases: Which Parameters Should Be Evaluated?." BioMed Research International 2015 (2015), 17 pages.
Golan et al., "Noninvasive Imaging of Flowing Blood Cells Using Label-Free Spectrally Encoded Flow Cytometry," Biomed Opt Express 3.6 (2012): 1455-1464.
Hofstee et al., "A Multicentre Study on the Reliability of Qualitative and Quantitative Nail-Fold Videocapillaroscopy Assessment," Rheumatology (2011): ker403, pp. 749-755.
Hollis et al., "Comparison of Venous and Capillary Differential Leukocyte Counts Using a Standard Hematology Analyzer and a Novel Microfluidic Impedance Cytometer," PloS One 7.9 (2012): e43702. 8 pages.
Hou et al., "A Computerized System of Nail-Fold Capillaroscopy for Dry Eye Disease Diagnosis." Multidimensional Systems and Signal Processing 23.4 (2012): 515-524.
Kim et al., "An Original Approach for Quantification of Blood Vessels on the Whole Tumour Section." Analytical Cellular Pathology 25.2 (2003): 63-75.
Lefford et al., "Nailfold Capillary Microscopy in Connective Tissue Disease: a Quantitative Morphological Analysis." Annals of the Rheumatic Diseases 45.9 (1986): 741-749.
MacLennan et al., "Finger-Prick Blood Samples Can Be Used Interchangeably With Venous Samples for CD4 Cell Counting Indicating Their Potential for Use in CD4 Rapid Tests," AIDS 21.12 (2007), 7 pages.

PCT International Search Report and Written Opinion for International Application No. PCT/US2018/056100 dated Mar. 7, 2019, eleven (11) pages.
PCT International Search Report and Written Opinion for International Application No. PCT/US2020/034483 dated Aug. 4, 2020, eleven (11) pages.
PCT International Search Report and Written Opinion for International Application No. PCT/US2015/062487 dated Feb. 5, 2016, thirteen (13) pages.
Deneux et al., "A processing work-flow for measuring erythrocytes velocity in extended vascular networks from wide field high-resolution optical imaging data." Neuroimage 59.3 (2012): 2569-2588.
Doshi et al., "Computer-Aided Analysis of Nailfold Capillaroscopy Images." Handbook of Research on Trends in the Diagnosis and Treatment of Chronic Conditions. IGI Global, 2016. 146-158.
Supplementary European Search Report for Application No. EP 15 86 2463, dated Sep. 11, 2018, seven (7) pages.
Grassi et al., "Capillaroscopy: questions and answers." Clinical Rheumatology 26.12 (2007): 2009, (eight (8) pages).
Written Opinion of the International Searching Authority for International Application No. PCT/US2021/034455, dated Sep. 21, 2021, eight (8) pages.
McKay et al., "Imaging Human Blood Cells In Vivo With Oblique Back-Illumination Capillaroscopy." Biomedical Optics Express 11.5 (2020): 2373-2382.
McKay et al., "Visualization of Blood Cell Contrast In Nailfold Capillaries With High-Speed Reverse Lens Mobile Phone microscopy." Biomedical Optics Express 11.4 (2020): 2268-2276.
Mercer et al., "Quantitative Nailfold Video Capillaroscopy In Patients With Idiopathic Inflammatory Myopathy." Rheumatology 49.9 (2010): 1699-1705.
Moeini, Mohammad, et al. "Effects of Anesthesia on the Cerebral Capillary Blood Flow In Young and Old Mice." Multiphoton Microscopy in the Biomedical Sciences XV. vol. 9329. International Society for Optics and Photonics, 2015, 7 pages.
Murray et al., "The Influence of Measurement Location on Reliability of Quantitative Nailfold Videocapillaroscopy In Patients With SSc." Rheumatology 51.7 (2012): 1323-1330.
Pablo-Trinidad et al., "Automated Detection of Neutropenia Using Noninvasive Video Microscopy of Superficial Capillaries." American Journal of Hematology 94.8 (2019):. 5 pages.
Pennarola et al.,"Nailfold Capillroscopic Monitoring As Preventive Medicine In Subjects Exposed to Ionising Radiation." 11th International Congress of the International Radiation Protection Association. 2004. 6 pages.
Reif et al., "Label-Free Imaging of Blood Vessel Morphology With Capillary Resolution Using Optical Microangiography." Quantitative Imaging In Medicine and Surgery 2(3) (2012): 207-212.
Russcher et al., "Evaluation of the HemoCue WBC DIFF System For Point-Of-Care Counting of Total and Differential White Cells In Pediatric Samples," Ned Tijdschr Klin Chem Labgeneesk 38 (2013): 140-141.
Angela C. Shore, "Capillaroscopy and the Measurement of Capillary Pressure." British Journal of Clinical Pharmacology 50 (2000): 501-513.
Uji et al., "The Source of Moving Particles In Parafoveal Capillaries Detected By Adaptive Optics Scanning Laser Ophthalmoscopy," Investigative Ophthalmology & Visual Science 53.1 (2012): 171-178.
Winkelman et al., "Noninvasive Blood Cell Measurements By Imaging of the Microcirculation," Am J Clin Pathol 113 (2000): 479-483.
Wu, Chih-Chieh, et al. "Accuracy Evaluation of RBC Velocity Measurement In Nail-Fold Capillaries." Microvascular Research 81.3 (2011): 20 pages.
Yap et al., "Mechanical Deformation of Neutrophils Into Narrow Channels Induces Pseudopod Projection and Changes In Biomechanical Properties", Journal of Applied Physiology 98 (2005): 1930-1939.

* cited by examiner

METHOD TO DETECT WHITE BLOOD CELLS AND/OR WHITE BLOOD CELL SUBTYPES FROM NON-INVASIVE CAPILLARY VIDEOS

RELATED APPLICATIONS

This application claims benefit of and priority to U.S. Provisional Application Ser. No. 63/031,117 filed May 28, 2020, under 35 U.S.C. §§ 119, 120, 363, 365, and 37 C.F.R. § 1.55 and § 1.78, which is incorporated herein by this reference.

FIELD OF THE INVENTION

The subject invention relates to a method to detect white blood cells and/or white blood cell subtypes from non-invasive capillary videos. The subject invention also relates to a method to determine a density of red blood cells from non-invasive capillary videos.

BACKGROUND OF THE INVENTION

There is an acute clinical need for an improved, non-invasive, fast, accurate and reliable way to measure patients' white blood cells and white blood cell subtypes, including the identification of patients with dangerously low levels of white blood cells. White blood cells, also called leukocytes, include, inter alia, the white blood cell subtypes of neutrophils, lymphocytes, monocytes, eosinophils, and basophils. According to the Centers for Disease Control and Prevention, 110,000 of the 650,000 cancer patients treated with chemotherapy in the U.S. every year are hospitalized due to chemotherapy-induced febrile neutropenia, a clinically low level of neutrophils. See, e.g., Tai et al., *Cost of Cancer-Related Neutropenia or Fever Hospitalizations*, Journal of Oncology Practice, 13 (6) (2017), incorporated by reference herein. Such hospitalizations typically average 8.5 days, may have admission costs of about $25,000, and have a mortality rate of about seven percent, making neutropenia one of the most severe side effects of chemotherapy. See, e.g., Truong et al., *Interpreting Febrile Neutropenia Rates From Randomized Controlled Trials for Consideration of Primary Prophylaxis in The Real World: A Systematic Review and Meta-Analysis*, Annals of Oncology, 27 (4) (2015), and Lyman, et al., *Cost of Hospitalization in Patients With Cancer and Febrile Neutropenia and Impact of Comorbid Conditions*, Am. Soc. Hematology (2015), both incorporated by reference herein. There are also many other diseases and conditions associated with dangerously low levels of white blood cells, including Acquired Immunodeficiency Syndrome (AIDS), autoimmune diseases, organ transplantation, patients treated with immunosuppressant drugs for various conditions and the like.

One conventional technique which may be used to identify patients with dangerously low levels of white blood cells is a Complete Blood Count (CBC). The CBC can monitor white blood cells differentials and neutropenia. The invasive CBC requires drawing more than about 3 mLs of blood in a clinical setting. The subsequent lab analysis typically takes hours to several days for the results. The CBC is challenging and costly to perform, and potentially requires immunocompromised patients to visit a hospital, putting them at increased risk for developing an infection. See, e.g., Weinstein, R. A., *Nosocomial Infection Update*, Emerging Infectious Diseases, 4 (3), (1998), incorporated by reference herein.

Alternative conventional technologies based on finger pricks may have fundamental limitations because of a lack of repeatability between successive drops of blood, elevated leukocyte counts from fingertip blood at the site of puncture, and the blood obtained with such a method may include interstitial fluid. See e.g., Bond, et al., *Drop-to-Drop Variation in the Cellular Components of Fingerprick Blood: Implications for Point-of-are Diagnostic Development*, Am. J. Clin. Pathol., 144 (6) (2015), Yang et al., *Comparison of Blood Counts in Various Fingertip and Arterial Blood and Their Measurement Variation*, Clin. Lab. Haematol. 23 (3) (2001), Daae et al., *A Comparison Between Haematological Parameters in 'Capillary' and Venous Blood From Healthy Adults*, 48 (7) (1988), all incorporated by reference herein. With such limitations, fingerprick approaches may poorly represent systemic cell blood count when performed outside the clinical setting. See, e.g., Hollis et al., *Comparison of Venous and capillary Differential Leutkocyte Counts Using a Standard Hematology Analyzer and a Novel Microfluidic Impedance Cytometer*, PloS one, 7 (9) (2012), and Ghai, C. L., *A Textbook of Practical Physiology*, J.P. Medical Ld. (2012), both incorporated by reference herein. Consequently, there are currently no devices for at-home, self-administered monitoring of white blood cell count, such as neutrophil count.

Conventional in vivo cell imaging systems and methods which may be portable, inexpensive, and practical for point of care typically have insufficient depth of focus, contrast, or field of view to detect white blood cell subtypes. Conventional capillaroscopes may be utilized to collect videos or images of nailfold capillaries of healthy subjects. See e.g., Maldonado et al., *Nailfold Capillaroscopy in Diabetes Mellitus, Microvascular Research*, 112.41-46 (2017) and Mengko et al., *Morphological Characterization of Nailfold Capillaries*, Intelligent Technology and Its Applications (ISITIA) International Seminar, IEEE (2016), both incorporated by reference herein. Such conventional systems and methods may allow imaging of the capillary geometry and optical absorption gaps (OAGs) in microcirculation but may have technical limitations including, inter alia, depth of focus, contrast to neutrophils, and stability that may prevent the acquired videos from subsequent analysis. See, e.g., Bourquard et al., *Analysis of White Blood Cell Dynamics in Nailfold Capillaries*, $37^{th}$ Annual International Conference of the IEEE Engineering in Medicine and Biology Society (EMBC), IEEE, (2015) and Bourquard et al., *Non-Invasive Detection of Severe Neutropenia in Chemotherapy Patients By Optical Imaging of Nailfold Microcirculation*, Sci. Rep, 8 (1):5301 (2018), both incorporated by reference herein. As defined herein, an "optical absorption gap" (OAG) is as an area within a capillary that is depleted of red blood cells and does not absorb light at the wavelengths at which absorption occurs in hemoglobin (e.g. about 400 nm to about 600 nm). An OAG may be created by the presence of any white blood cell subtype or by a plasma gap. See, e.g., U.S. Pat. No. 9,984,277 and U.S. Publ. No. 2019/0139221, both incorporated by reference herein. As disclosed in the '277 patent and the '221 patent application, videos or images of one or more capillaries may be used to show the frequency of OAGs flowing in a capillary correlates to white blood cells flowing in the capillary and may be used to determine white blood cell count. However, the '277 patent and the '221 patent application are limited to utilizing absorption signals and white blood cell subtypes within the OAGs cannot be identified and plasma gaps may also contribute to false positives or inaccurate quantitative measurement of white blood cell counts. See, e.g., Pablo-Trinidad et al., *Automated*

*Detection of Neutropenia Using Noninvasive Video Microscopy of Superficial Capillaries*, American Journal of Hematology, 94 (8) (2019), McKay et al., *Visualization of Blood Cell Contrast in Nailfold Capillaries With High-speed Reverse Lens Mobile Phone Microscopy*, Biomedical Optical Express, 11 (4) (2020), and McKay et al., *Optimizing White Blood Cell Contrast in Graded-Field-Capillaroscopy Using Capillary Tissue Phantoms*, Imaging, Manipulation, and Analysis of Biomolecules, Cells, and Tissues, International Society for Optics and Photonics XVIII, Vol. 11243 (2020), all incorporated by reference herein.

The conventional in vivo cell imaging systems and methods, the '277 patent, and the '221 patent application discussed above are also unable to determine density of red blood cells which may be used to non-invasively determine RBC count.

SUMMARY OF THE INVENTION

In one aspect, a method to detect white blood cells and/or white blood cell subtypes from non-invasive capillary videos is featured. The method includes acquiring a first plurality of images of a region of interest including one or more capillaries of a predetermined area of a human subject from non-invasive capillary videos captured with an optical device, processing the first plurality of images to determine one or more optical absorption gaps located in said capillary and annotating the first plurality of images with an indication of any optical absorption gap detected in the first plurality of images. The method also includes acquiring a second plurality of images of the same region of interest of the same capillary with an advanced optical device capable of resolving cellular structure of white blood cells and white blood cell subtypes and spatiotemporally annotating the second plurality of images with an indication of any white blood cell detected and/or a subtype of any white blood cell detected in the second plurality of images. The method also includes inputting the first plurality of images and annotated information from the first plurality of images and annotated information from the spatiotemporally annotated second plurality of images into a machine learning subsystem configured to determine a presence of white blood cells and/or the subtype of any white blood cells present in the one or more optical absorption gaps in the first plurality of images.

In one embodiment, the machine learning subsystem may be further configured to determine a white blood cell subtype for any optical absorption gap detected in the first plurality of images. The machine learning subsystem may be further configured to determine full white blood cell differential measurements and/or partial white blood cell differential measurements. The method may further include temporally aligning the first plurality of images to the spatiotemporally annotated second plurality of images. The temporal aligning may include creating said region of interest and said same region of interest by using a same objective lens on the optical device and the advanced optical device. The temporally aligning may include creating said region of interest and said same region of interest by focusing the optical device and the advanced optical device at a same location in the capillary. The method may further include generating optical absorption gap reference data including a frame identifier and indication of any optical absorption gap detected in the first plurality of images. The method may further include generating spatiotemporally annotated lookup data including a frame identifier and indication of the subtype of any white blood cell present. Temporally aligning the first plurality of images to the spatiotemporally annotated second plurality of images may include temporally aligning the frame identifier of the first plurality of images to the frame identifier of the visually spatiotemporally annotated second plurality of images. The method may further include inputting the first plurality of images, the optical absorption gap reference data, and the spatiotemporally annotated lookup data into the machine learning subsystem. The machine learning subsystem may be configured to output results data of any white blood cells detected and/or the subtype of any white blood cells detected and compare the results table to ground truth data. The machine learning subsystem may be configured to output results data of any white blood cells detected and/or a subtype of any white blood cells detected for each optical absorption gap in the first plurality images and compare the results data to a ground truth data. Spatiotemporally annotating the second plurality of images may further include indicating one or more of: a size, a granularity, a brightness, a speed, an elongation, and/or a margination of the white blood cells and/or a change of density of red blood cells located upstream or downstream from a location of white blood cells detected. The subtype of the white blood cell may include a granulocyte, a neutrophil, a lymphocyte, a monocyte, an eosinophil or a basophil. The optical device may include a high-resolution camera. The advanced imaging device may include, inter alia, one or more of: a spectrally-encoded confocal microscopy (SECM) device, a swept confocally-aligned planar excitation (SCAPE) microscopy device, a scattering confocally aligned oblique plane imaging (SCOPI) device, or oblique back-illumination microscopy (OBM) device. The predetermined area of the human subject may include, inter alia, one or more of: a finger, a nailfold, a toe, a tongue, a gum, a lip, a retina, and/or an earlobe. The optical device may be configured to output at least one optical absorption gap signal. The advanced optical device may be configured to output an advanced optical signal. Spatiotemporally annotating the second plurality of images may be performed by a human. Spatiotemporally annotating the second plurality of images may be performed by a processing subsystem. The method may further include determining the presence of white blood cells and/or the subtype of any white blood cells present in the one or more optical absorption gaps using the first plurality of images and annotated information from the first plurality of images and information from the machine learning subsystem which has learned and determined the presence of white blood cells and/or the subtype of white blood cells present in one or more optical absorption gaps using the annotated information from the second plurality of images acquired with the advanced optical device.

In another aspect, a method to detect white blood cells and/or white blood cell subtypes from non-invasive capillary videos is featured. The method includes acquiring a first plurality of images of a region of interest including one or more capillaries of a predetermined area of a human subject from non-invasive capillary videos captured with an optical device, processing the first plurality of images to determine one or more optical absorption gaps located in said capillary, and annotating the first plurality of images with an indication of any optical absorption gap detected in the first plurality of images. The method also includes determining a presence of white blood cells and/or the subtype of any white blood cells present in the one or more optical absorption gaps using the first plurality of images and annotated information from the first plurality of images and information from a machine learning subsystem which has learned and determined the presence of white blood cells and/or the subtype of white blood cells present in one of more optical absorption gaps using annotated information from a second plurality of images acquired with the advanced optical device.

In yet another aspect, a method to determine a density of red blood cells from non-invasive capillary videos is featured. The method includes acquiring a first plurality of images of a region of interest including one or more capillaries of a predetermined area of a human subject from non-invasive capillary videos captured with an optical device, processing the first plurality of images to determine one or more areas of hemoglobin optical absorption located in the capillary, and annotating the first plurality of images with an indication of any areas of hemoglobin optical absorption detected in the plurality of images. The method also includes acquiring a second plurality of images of the same region of interest of the same capillary with an advanced optical device capable of resolving cellular structure of red blood cells, spatiotemporally annotating the second plurality of images with an indication of a density of any red blood cells detected in the second plurality of images, and inputting the first plurality of images and annotated information from the first plurality of images and annotated information from the spatiotemporally annotated second plurality of images into a machine learning subsystem configured to determine the density of any red blood cells present in the one or more optical absorption gaps in the first plurality of images.

In one embodiment, a red blood cell count may be determined from the density of red blood cells.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
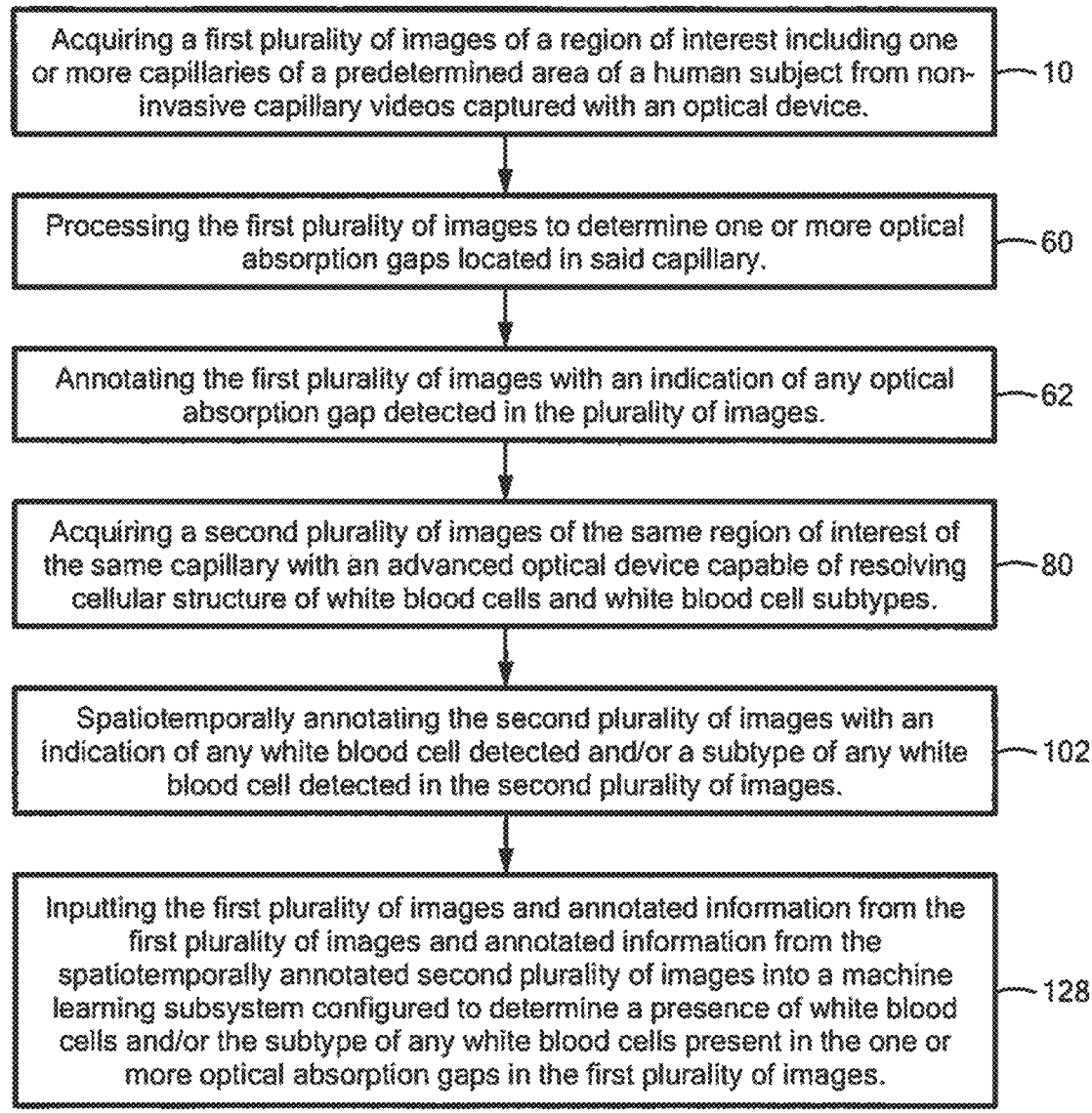
FIG. 1 is a flowchart showing the primary steps of one embodiment of the method to detect white blood cells and/or white blood cell subtypes from non-invasive capillary videos.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 2:
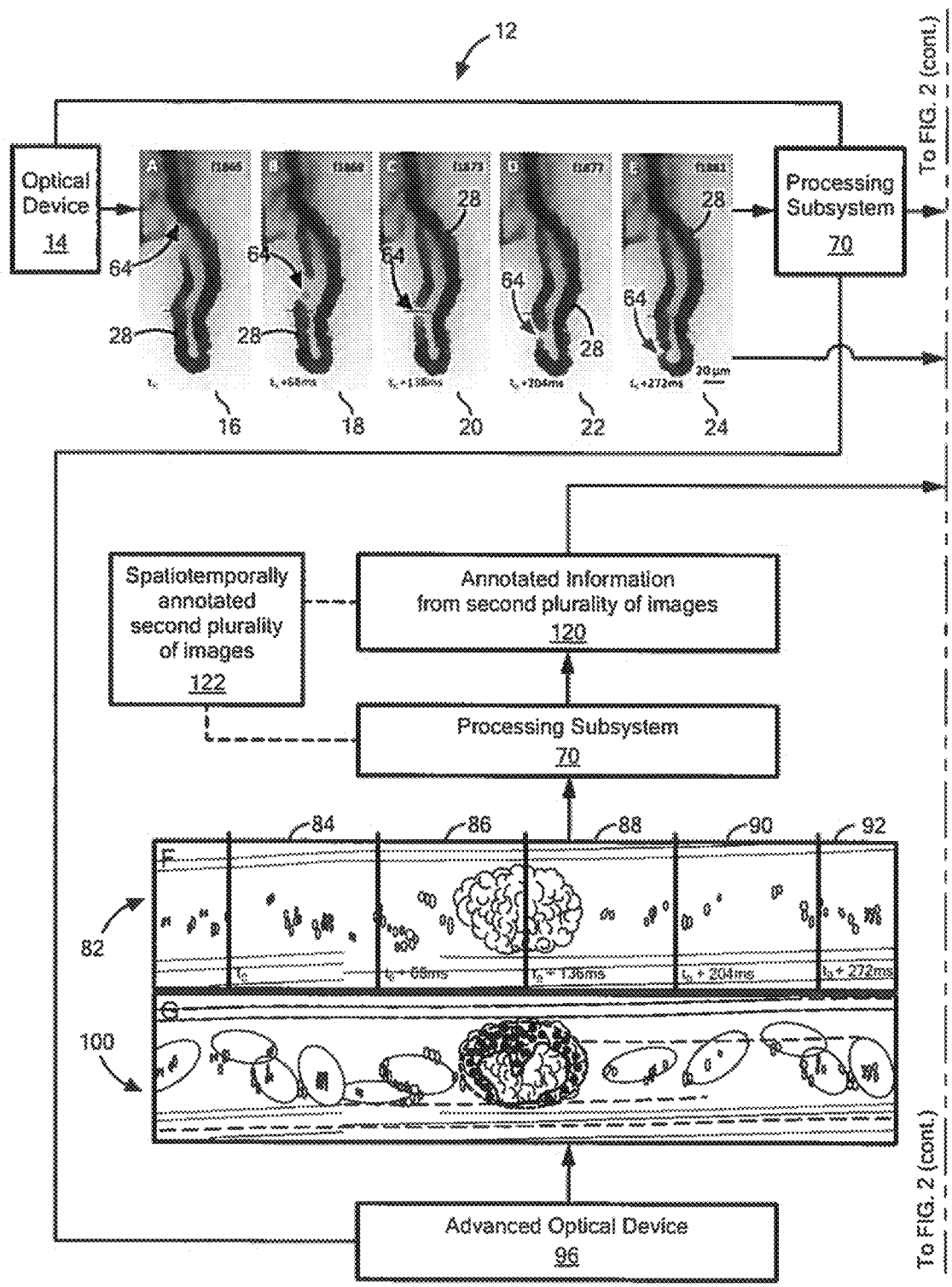
FIG. 2 shows in further detail examples of images of frames of the first plurality of images and the second plurality of images and additional components which may be utilized by the method shown in FIG. 1.
Figure 2:
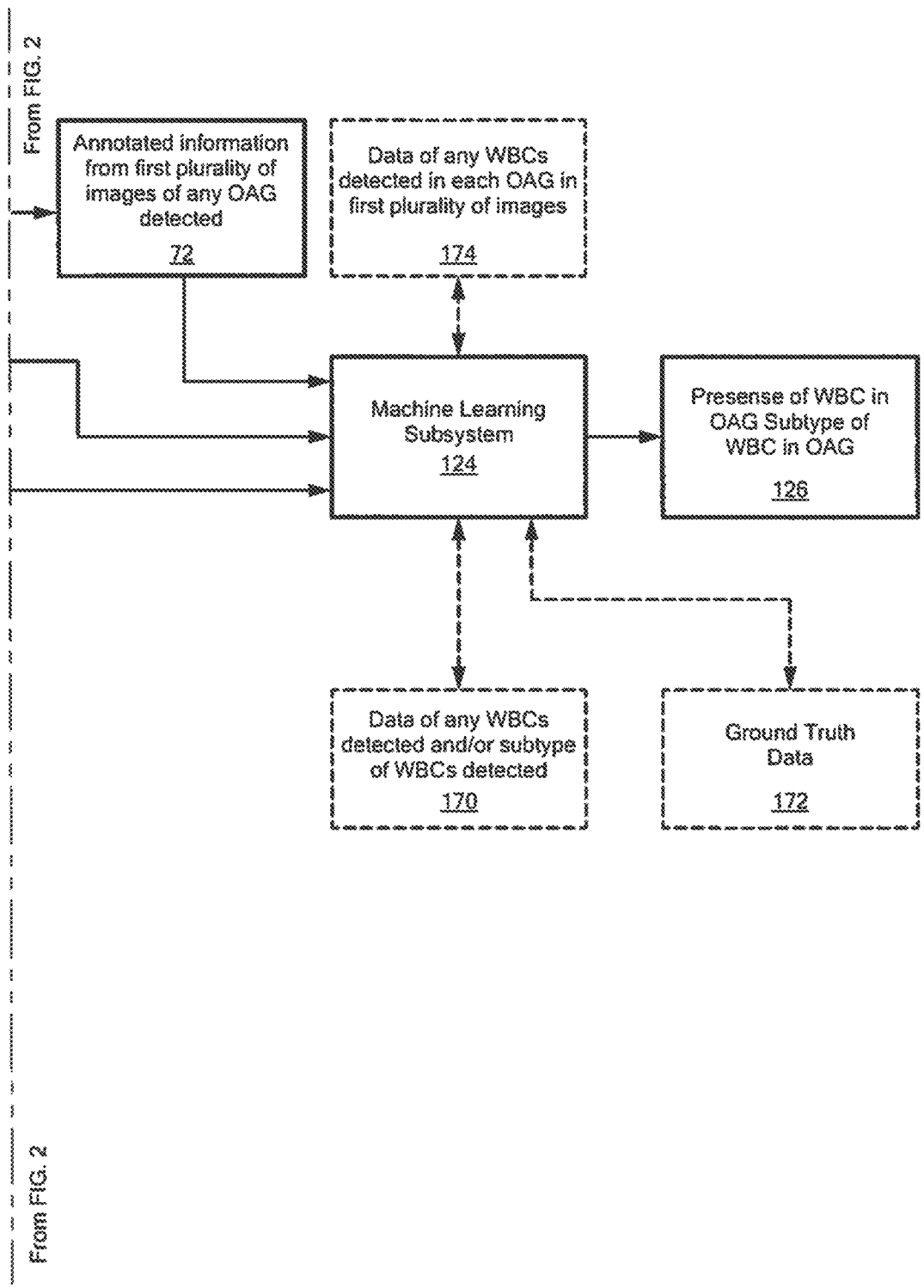
Figure 3:
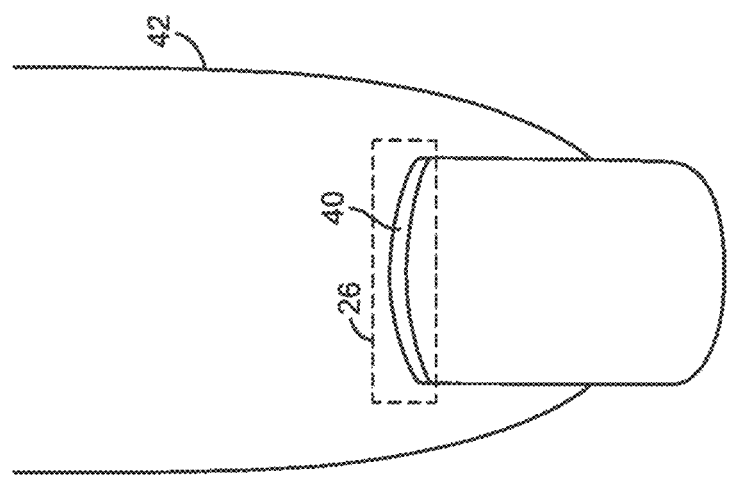
FIG. 3 is a schematic diagram showing one example of a nailfold of a finger of a human subject for the predetermined area of the human subject for the method shown in one or more of FIGS. 1 and 2.

There is shown in FIG. 1, one embodiment of the method to detect white blood cells and/or white blood cell subtypes from non-invasive capillary videos. The method includes acquiring a first plurality of images of a region of interest including one or more capillaries of a predetermined area of a human subject from non-invasive capillary videos captured with an optical device, step 10, FIG. 1. First plurality of images 12, FIG. 2, are preferably derived from non-invasive capillary videos acquired or captured with optical device 14, e.g., a high-resolution camera, an imager or imaging device as disclosed in the '277 patent and/or the '221 patent application cited supra and incorporated by reference, or similar type device. In this example, first plurality of images 12 includes images or frames 16, 18, 20, 22 and 24 of region of interest (ROI) 26, FIGS. 3 and 4, which includes one or more capillaries, e.g., capillary 28, FIGS. 2 and 4 of a predetermined area of a human subject. In this example, first plurality of images 12 includes five images or frames 16, 18, 20, 22, and 24. In other examples, first plurality of images 12 may include more or less than five images or frames 16-24 as depicted in this example. In one example, the predetermined area of the human subject may be the nailfold of a finger, e.g., nailfold 40, FIG. 3, of finger 42 of human subject 44, FIG. 5. Nailfold 40, FIG. 3, is one preferred area of the human subject because one or more capillaries are more easily detected by optical device 14 because the capillaries are in a more longitudinal position, e.g., as shown by capillary 28, FIG. 6. In other examples, the predetermined area of human subject 44, FIG. 5, may include a toe, a tongue, a gum, a lip, a retina, an earlobe, or any similar body part determined area of human subject 44.

Figure 4:
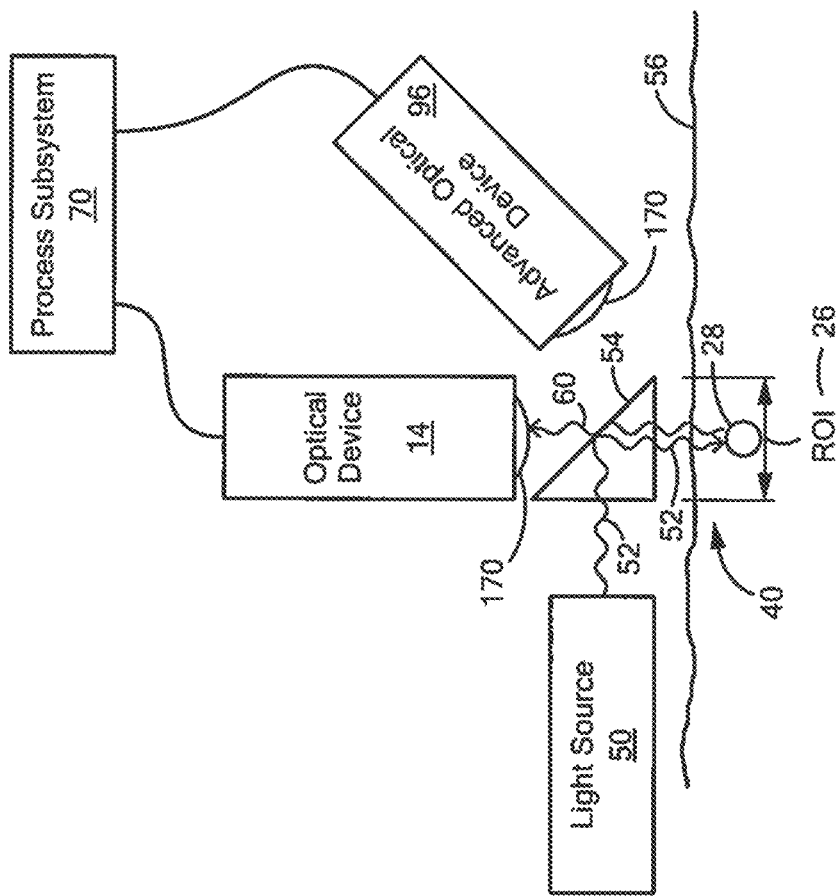
FIG. 4 is a schematic diagram showing in further detail examples of additional components utilized by the method shown in one or more of FIGS. 1-3 and an example of a region of interest.
Figure 5:
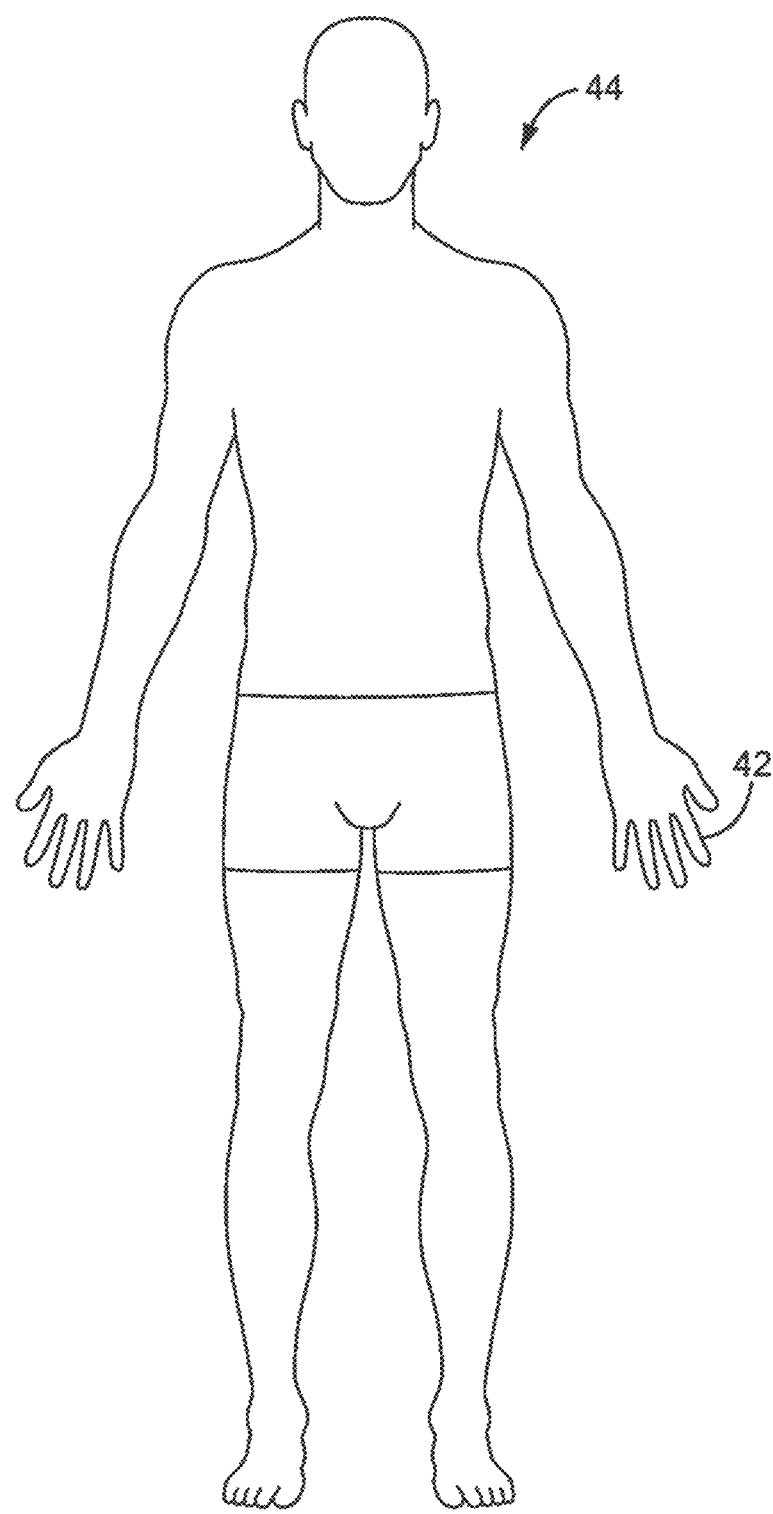
FIG. 5 shows examples of additional areas of the predetermined area of a human subject utilized for the method shown in one or more of FIGS. 1-4.

FIG. 4 shows in further detail one example of ROI 26 of a predetermined area of the human subject where images of one or more capillaries may be acquired or captured with optical device 14. As disclosed in the '221 patent application and/or the '277 patent, in one design, a light source 50 emits light 52 which is reflected by mirror 54 such that light 52 penetrates nailfold 56 of 40 in ROI 26 and reflected light 60 is detected by optical device 14 coupled to processing subsystem 70, FIGS. 2 and 4, to create non-invasive capillary videos which include first plurality of images 12, FIG. 2, with images or frames 16-24.

The method to detect white blood cells and/or white blood cell subtypes from non-invasive capillary videos also includes processing first plurality of images 12 to determine one or more OAGs located in the capillary, step 60. FIG. 1. As discussed in the Background Section above, an OAG is an area within a capillary that is depleted of red blood cells and does not absorb light at the wavelengths at which absorption occurs in hemoglobin (e.g., about 400 nm to about 600 nm) and indicates the presence of one or more white blood cells, e.g., as disclosed in the '221 patent application and/or the '277 patent. In one example, processing subsystem 70 coupled to optical device 14, similar to the processor disclosed in the '221 patent application and/or the '277 patent, or similar type processing subsystem, processes first plurality of images 12 and detects one or more OAGs, e.g., OAGs 64, FIG. 2, in capillary 28 in images or frames 16, 18, 20, 22, and 24.

The method to detect white blood cells and/or white blood cell subtypes from non-invasive capillary videos also includes annotating the first plurality of images 12 with an indication of any OAG detected in the plurality of images, step 62, FIG. 1. In one example, first plurality of images 12, FIG. 2, are input to processing subsystem 70 which outputs annotated information 72 associated with any OAG detected. In one example, annotated information 72 preferably includes OAG reference data, e.g., OAG reference table 74, FIG. 7, or similar type OAG reference data, that preferably includes frame identifier 76 and an indication of any optical gap detected in each of images or frames 16, 18, 20, 22, and 24 of the first plurality of images 12, indicated at 78. In this example, OAG reference table 74 includes frame identifiers $t_0, t_1, t_2, t_3, t_4 \ldots t_n$, for each image or frame and an OAG identifier for each image or frame, e.g., a 1 to indicate an OAG has been detected. Annotating first plurality of images 12, FIGS. 2 and 7, with an indication of any OAG detected in first plurality of images 12 to generate annotated information 72 may be performed by a trained human operator or by processing subsystem 70, FIGS. 2 and 4.

The method to detect white blood cells and/or white blood cell subtypes from non-invasive capillary videos also includes acquiring a second plurality of images of the same region of interest of the same capillary with an advanced optical device capable of resolving cellular structure of white blood cells and white blood cell subtypes, step 80, FIG. 1.

Figure 6:
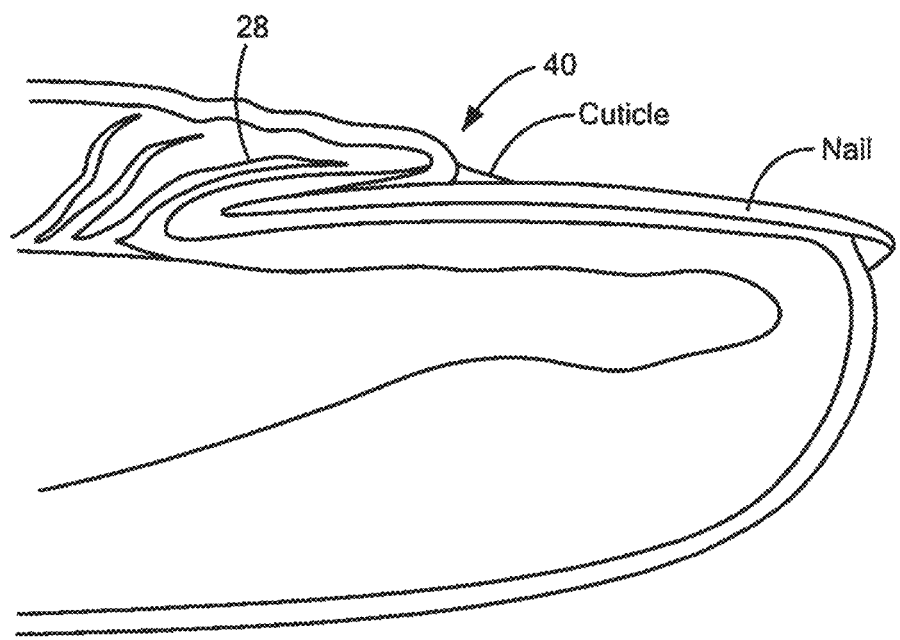
FIG. 6 shows in further detail an example of one or more capillaries of the nailfold shown in FIG. 3 that may be detected by an optical device for the method shown in one or more of FIGS. 1-5.

FIG. 2 shows one example of second plurality of images 82 which includes images or frames 84, 86, 88, 90, 92, and 94 of the same ROI 26, FIGS. 3 and 4, which includes one or more capillaries, e.g., capillaries 28 of a predetermined area of the human subject, e.g., nailfold 40, acquired or captured with advanced optical device 96, FIGS. 2 and 6, capable of resolving cellular structure of white blood cells and white blood cell subtypes. In one example, advanced optical device 96 may include a spectrally-encoded confocal microscopy (SECM) device, a swept confocally aligned planar excitation (SCAP) microscopy device, a scattering confocally aligned oblique plane imaging (SCOPI) device, or an oblique black illumination microscopy (OBM) device, e.g., as disclosed in Golan et al., *Noninvasive Imaging of Flowing Blood Cells Using Label-Free Spectrally Encoded Flow Cytometry*, Biomedical Optics Express, Vol. 3 No. 6 (2012), Bouchard et al., *Swept Confocal-Aligned Planar Excitation (SCAP) Microscopy for High-Speed Volumetric Imaging of Behaving Organisms*, Nature Photonics, Vol. 9 (2015), McKay et al., *High-Speed Imaging of Scattering Particles Flowing Through Turbid Media With Confoncially Aligned, Oblique Plane Illumination*, SPIE Bios, San Francisco, CA (2019), McKay et al., *Imaging Human Blood Cells In Vivo With Oblique Back-Illumination Capillaroscopy*, Biomedical Optics Express, Vol. 11 (5) (2020), and Ford, T., N. and Mertz, J., *Video-Rate Imaging of Microcirculation With Single-Exposed Oblique Black Illumination Microscopy*, Journal of Biomedical Optics, Vol. 18 (6) (2013), all incorporated by reference herein.

In one example, the cellular structure of white blood cells and white blood cell subtypes resolved by advanced optical device 96 may include the subtype of any white blood cells detected, e.g., a granulocyte, a neutrophil, a lymphocyte, a monocyte, an eosinophil, or a basophil. Image 100, FIG. 2, shows one example of the cellular structure of a white blood cell and/or white blood cell subtype in images 86 and 88 resolved by advanced optical device 96, e.g., in this example, resolved by a spectrally-encoded confocal microscopy (SECM) or similar type advanced optical device.

The method to detect white blood cells and/or white blood cell subtypes from non-invasive capillary videos also includes spatiotemporally annotating second plurality of images with an indication of any white blood cell detected and/or a subtype of any white blood cell detected in the second plurality of image, step 102, FIG. 1. Spatiotemporally annotating the second plurality of images 82, FIG. 2, may include indicating one or more of a size, a granularity, a brightness, a speed, an elongation, and/or a margination of any white blood cells detected and/or a change in density of red blood cells located upstream or downstream from the location of any white blood cells detected. In one example, second plurality of images 82, FIG. 2, is spatially annotated using spatiotemporally annotated data, e.g., spatiotemporally annotated look-up table 108, FIG. 7, that includes frame identifier 110, e.g., $t_0, t_1, t_2, t_3, t_4 \ldots t_n$ for each of images or frames 84, 86, 88, 90, 92, and an indication of the white blood cell subtype associated with each frame identifier, e.g., a granulocyte, a neutrophil, a lymphocyte, a monocyte, an eosinophil, or a basophil, exemplary indicated at 112. Spatiotemporally annotating second plurality of images 82 with an indication of any white blood cell detected and/or a subtype of any white blood cell detected in the second plurality of image 82 may be performed by a trained human operator or by processing subsystem 70, FIGS. 2 and 4, and preferably generates annotated information 120, FIG. 2, associated with second plurality of images 82, and spatiotemporally annotated second plurality of images 122.

The method to detect white blood cells and/or white blood cell subtypes also includes inputting first plurality of images 12, FIG. 2, annotated information 72 from the first plurality of images 12 and annotated information 120 from spatiotemporally annotated second plurality of images 122 into machine learning subsystem 124 configured to determine a presence of white blood cells and/or subtype of any white blood cells present in the one or more optical absorption gaps in the first plurality of images 12, step 128, FIG. 1. In one example, machine learning subsystem 124 may be neural network a support vector machine, a machine learning subsystem utilizing a Random Forest learning method, an AdaBoost meta-algorithm, a Naïve Bayes classifier, or deep learning, as known by those skilled in the art. Preferably, machine learning subsystem 122 may be configured to determine the presence of white blood cells in OAGs and determine a full white blood cell differential measurements and/or partial white blood cell differential measurements.

In one example, first plurality of images 12, FIG. 2, is preferably temporally aligned with spatiotemporally annotated second plurality of images 122. In this example, temporally aligning includes creating the same region of interest, e.g., ROI 26, FIGS. 2 and 4, using the same objective lens 170 on both optical device 14 and advanced optical device 96, FIG. 4. In other examples, temporally aligning first plurality of images 12 with spatiotemporally annotated second plurality of images 122 includes creating the same ROI 26 for optical device 14 and advanced optical device 96, FIG. 4, e.g., by focusing optical device 28 and advanced optical device 90 at the same location in the capillary, e.g., focusing on ROI 26 and capillary 28, as shown. In other examples, temporally aligning first plurality of images 12 with spatiotemporally annotated second plurality of images 122 may use image alignment processing methods, e.g., registration or similar image alignment processing methods as known by those skilled in the art. See e.g., Oliveira, F. P. and Travares, J. M. R., et al., *Medical Image Registration: A Review*, Computer Methods in Biomechanics and Biomedical Engineering, 17 (2) (2014), incorporated by reference herein.

In one embodiment, the method to detect white blood cells and/or white blood cell subtypes from non-invasive capillary videos preferably includes aligning first plurality of images 12, FIG. 2, to spatiotemporally annotated second plurality of images 122. In one example, temporally aligning first plurality of images 12 with spatiotemporally annotated second plurality of images 122 includes aligning each frame identifier 76, FIG. 7, e.g., $t_0, t_1, t_2, t_3, t_4 \ldots t_n$, in optical absorption gap reference table 74 to each frame identifier 110, e.g., $t_0, t_1, t_2, t_3, t_4 \ldots t_n$, in spatiotemporally annotated look-up table 108.

Figure 8:
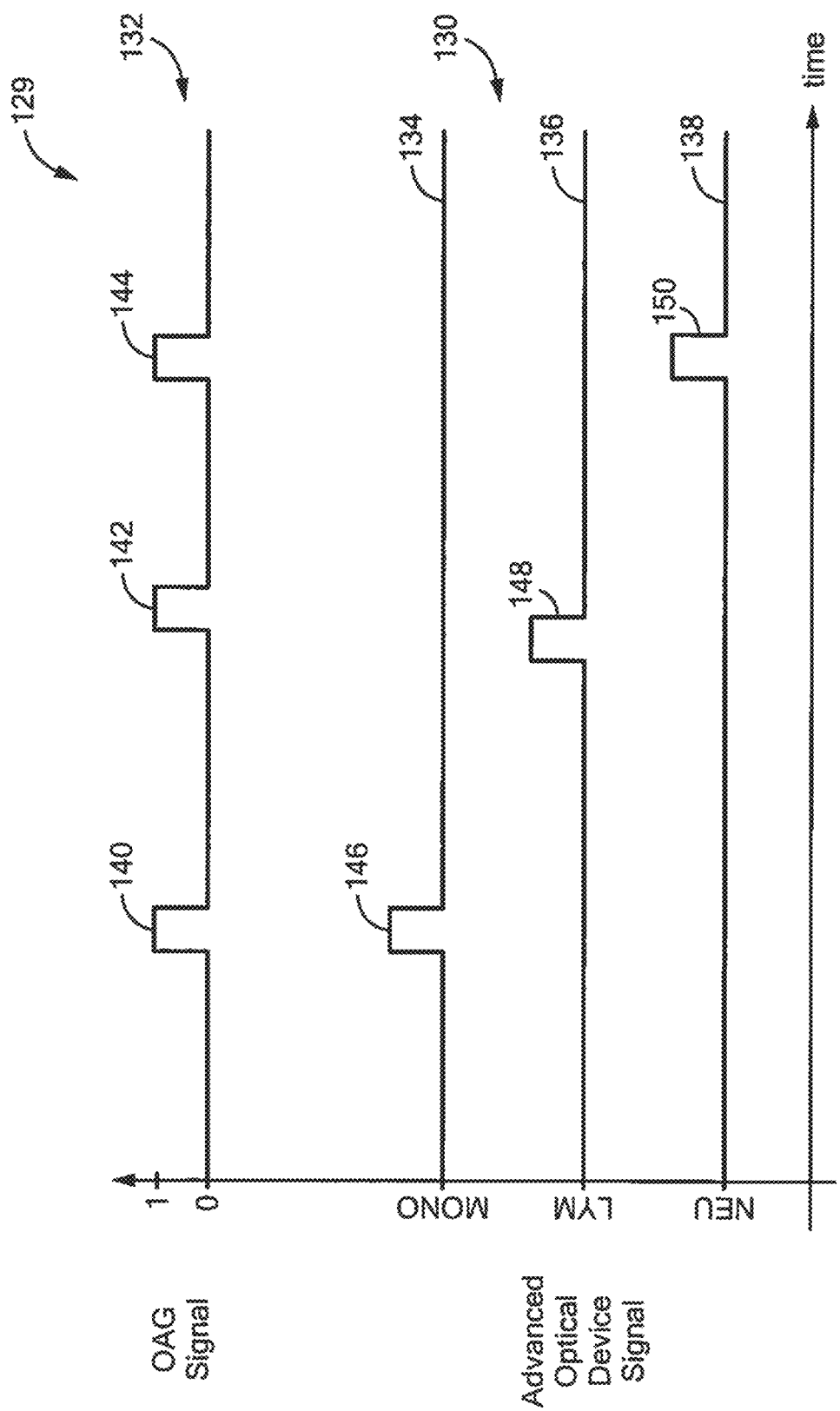
FIG. 8 shows examples of plots of OAG signals output by an optical device and plots of advanced optical output signals output by an advanced optical device for the method shown in one or more of FIGS. 1-7.

Plots 129, FIG. 8, show one example of OAG signal 132 output by optical device 14, FIGS. 2 and 4, and input to processing subsystem 70. In this example, OAG signal 132 includes peaks 140, 142, and 144 which each indicate the presence of an OAG indicative of a white blood cell in a capillary e.g., OAG 64, FIGS. 2 and 9, in capillary 28. Plots 129, FIG. 8, also show an example of advanced optical output signals 134, 136, and 138 output by advanced optical device 96, in this example a SECM device, which are input to processing subsystem 70, FIGS. 2 and 4. Each of advanced optical signals 134, 136, and 138 preferably include a peak that indicates the subtype of a white blood cell that corresponds to the presence or detection OAG in a capillary. For example, peak 146 of advanced optical signal 134 indicates a white blood cell subtype of a monocyte, peak 148 indicates a white blood cell subtype of a lymphocyte, and peak 150 indicates a white blood cell subtype of a granulocyte, a neutrophil. Peaks 146, 148, and 150 of advanced optical signals 134, 136, and 138, respectively, are for exemplary purposes only, as advanced optical signals 134, 136, and 138 may have peaks which represent other types of white blood cell subtypes. Plots 129 may also include additional advanced optical signals with peaks indicating additional white blood cell subtypes, e.g., eosinophils, basophils, or other white blood cellular structures. In this example, processing subsystem 70 temporarily aligns peak 146 of advanced optical signal 134 with peak 140 of OAG signal 132 as shown which indicates a monocyte is present in OAG 64, FIGS. 2 and 9, in capillary 28. Similarly, processing subsystem 70 temporarily aligns peak 148 of advanced optical signal 136 with peak 142 of OAG signal 132 as shown which, in this example, indicates a lymphocyte is present in OAG 64 in capillary 28. Processing subsystem 70 also temporarily aligns peak 150 of advanced optical signal 138 with peak 144 of OAG signal 132 as shown which indicates a neutrophil is present in OAG 64 in capillary 28. In a similar manner, processing subsystem 70 may temporarily align a peak of one or more additional advanced optical signals each having a peak indicating additional white blood cell subtypes, e.g., granulocyte, eosinophils, basophils, or other white blood cell structures with additional peaks on OAG signal 132.

Figure 9:
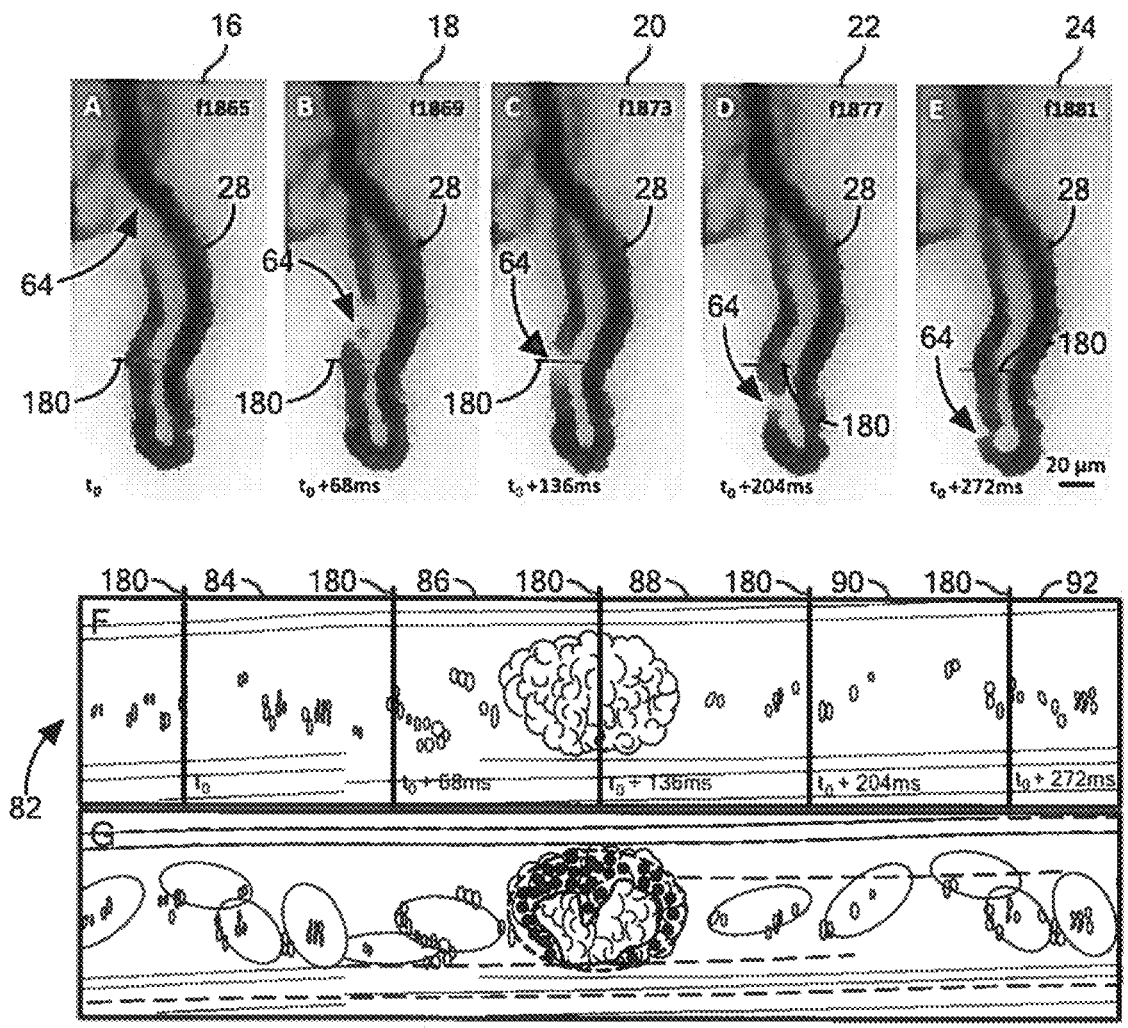
FIG. 9 shows in further detail examples of the first plurality of images with frame identifiers and the second plurality of images with frame identifiers that are temporally aligned for the method shown in one or more of FIGS. 1-8.

FIG. 9 shows one example of first plurality of images 12 with images of frames 16, 18, 20, 22, and 24 at frame identifiers, $t_0, t_{0+68\ ms}, t_{0+136\ ms}, t_{0+204\ ms}$, and $t_{0+272\ m}$, respectively, and second plurality of images 82 with images or frames 84, 86, 88, 90, and 92 at frame identifies $t_0, t_{0+68\ ms}, t_{0+136\ ms}, t_{0+204\ ms}$, and $t_{0+272\ m}$, respectively, which are temporarily aligned as shown. In this example advanced optical device 96, FIGS. 2 and 4, acquires second plurality of images 82, FIG. 9, using an SECM device that utilizes a line scan of capillary 28, indicated at 180. Other advanced optical devices may be used as disclosed above.

Figure 7:
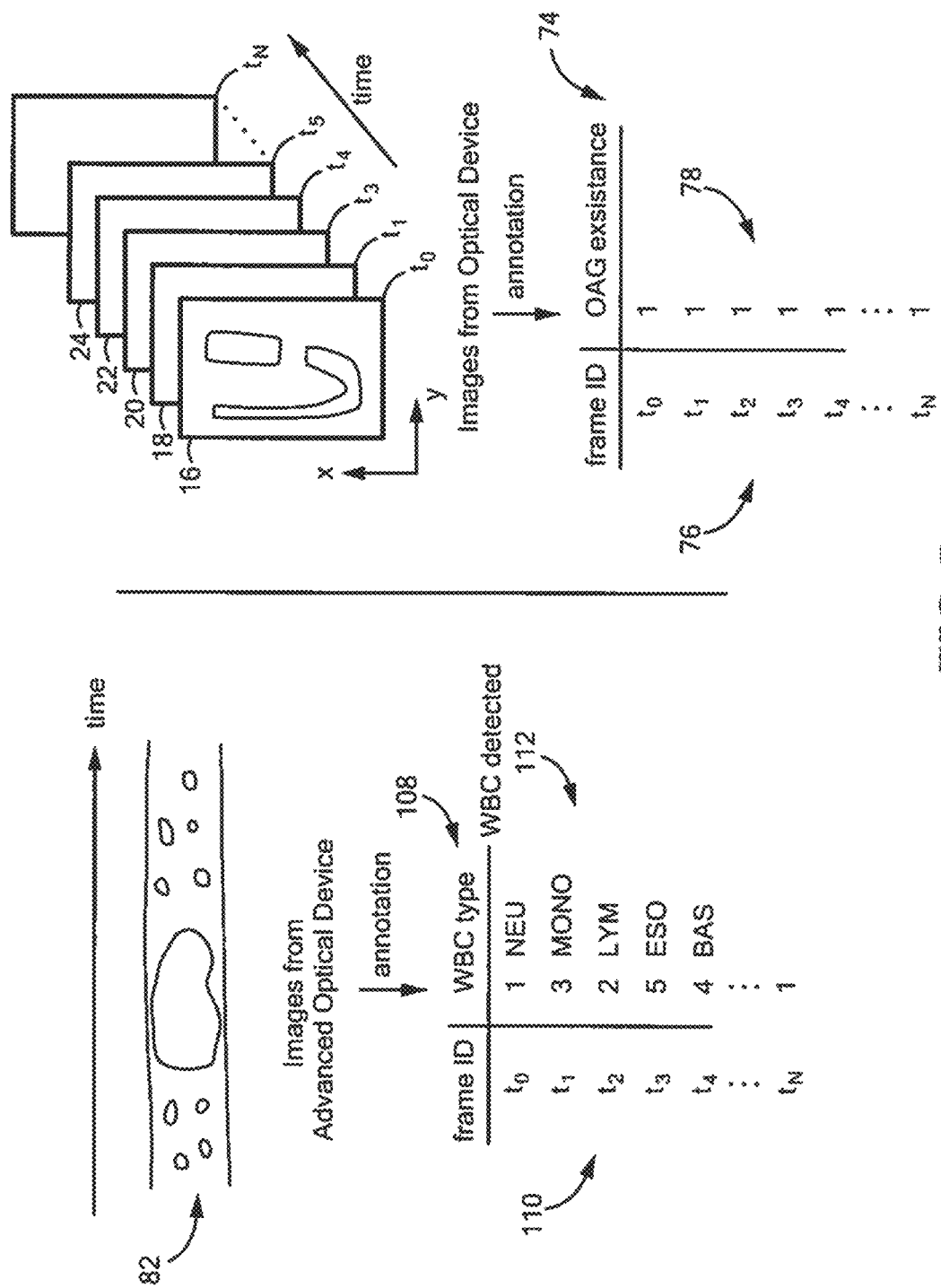
FIG. 7 shows an example of an OAG reference table for images detected with an optical device and then annotated and an example of a spatiotemporally annotated lookup table for images detected by an advanced optical device and then spatiotemporally annotated for the method shown in one or more of FIGS. 1-6.

In one example, first plurality of images 12, FIG. 2, annotated information 72 from the first plurality of images, e.g., OAG reference data 74, FIG. 7, e.g., a table or similar type data and annotated information from the second plurality of images 120. FIG. 2, e.g., spatiotemporally annotated look-up data 108, FIG. 7, e.g., a table or similar type data are input to machine learning subsystem 124, FIG. 2, which outputs results data 170, e.g., a table of similar type results data, which indicates any white blood cell detected and/or the subtype of any white blood cell detected. Machine learning subsystem 124 then preferably compares results data 170 to ground truth data 172, e.g., a table or similar type data to determine and improve the accuracy of the white blood cells detected and/or the white blood cell subtypes determined. As known by those skilled in the art, "ground truth" is a term relative to the knowledge of the truth concerning an ideal expected result.

In one embodiment, machine learning subsystem 122 may output results data 174, e.g., a table of similar type data, that includes any white blood cells detected and/or a subtype of any white blood cells detected for each OAG in first plurality of images 12 and compares results data 174 to ground truth data 172 data to determine and improve the accuracy of the white blood cells detected and/or the white blood cell subtypes determined.

Figure 10:
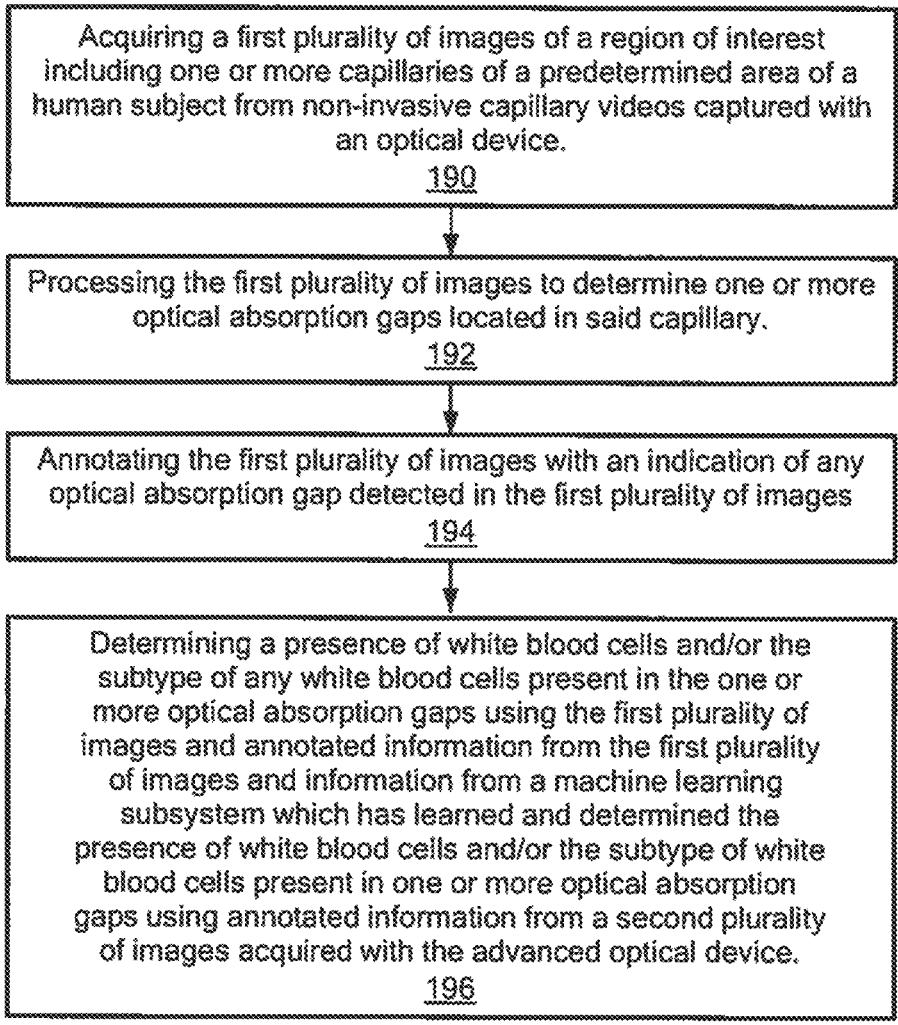
FIG. 10 is a flowchart showing another embodiment of the method to detect white blood cells and/white blood cell subtypes from non-invasive capillaries.
Figure 11:
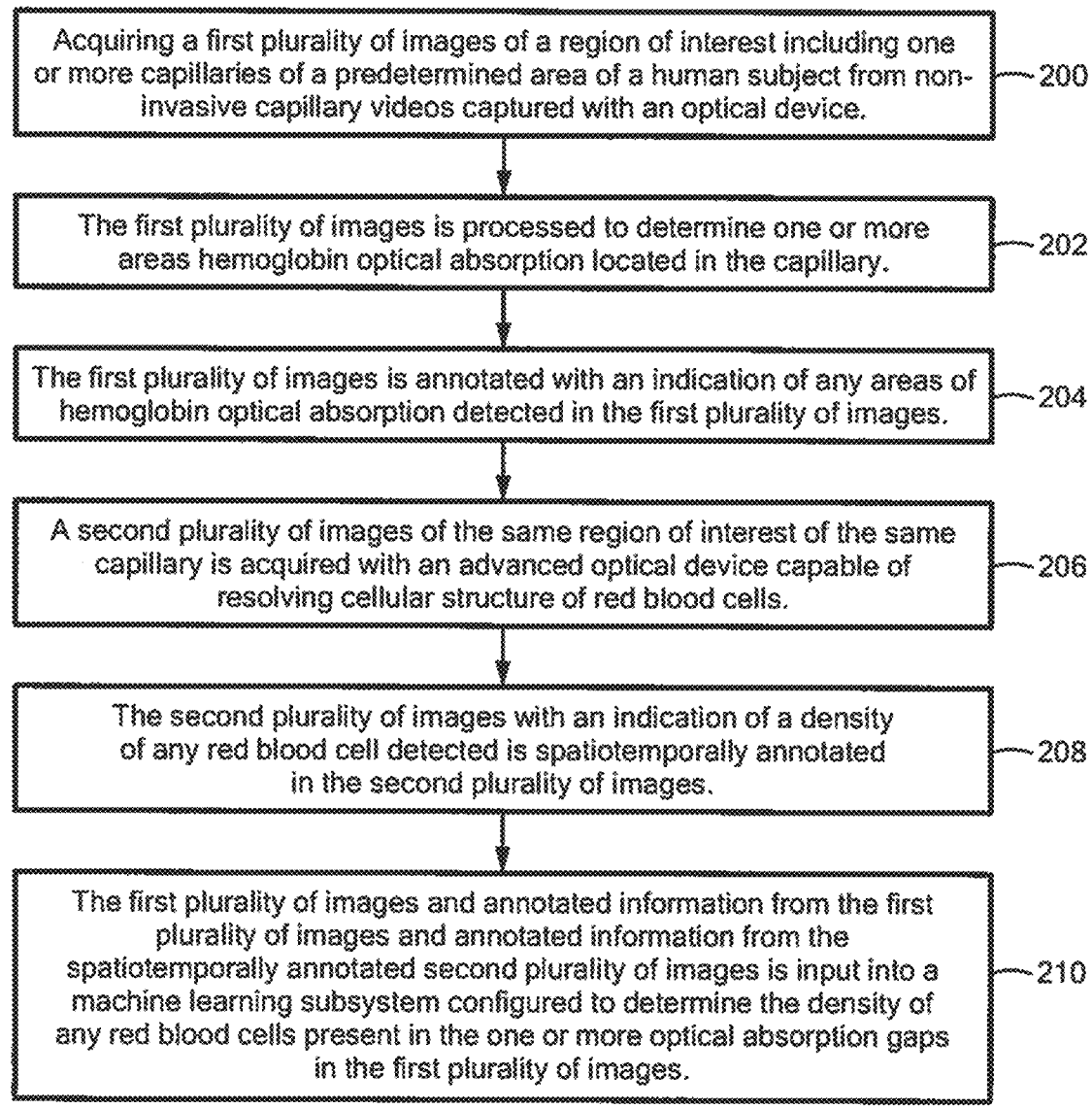
FIG. 11 is a flowchart showing one embodiment of the method to determine the density of any red blood cells present in one or more adsorption gaps.

Once machine learning subsystem 124, FIG. 2, efficiently and effectively learns and determines the presence of white blood cells and/or the subtype of white blood cells present in one or more optical absorption gaps using the annotated information from the second plurality of images acquired with the advanced optical device, the method to detect white blood cells and/or white blood cell subtypes from non-invasive capillaries of another embodiment using similar techniques as discussed above with reference to one or more of FIGS. 1-9, may include acquiring a first plurality of images of a region of interest including one or more capillaries of a predetermined area of a human subject from non-invasive capillary videos captured with an optical device, step 190, FIG. 10. The method may also include processing the first plurality of images to determine one or more optical gaps located in the capillary, step 192. The method may also include annotating the first plurality of images with an indication of any optical gap detected in the first plurality of images, step 92, and determining a presence of white blood cells and/or the subtype of any white blood cells present in the one or more optical absorption gaps using the first plurality of images and annotated information from the first plurality of images and information from a machine learning subsystem which has learned and determined the presence of white blood cells and/or the subtype of white blood cells present in one or more optical absorption gaps using annotated information from a second plurality of images acquired with an advanced optical device, step 194.

The result is the method to detect white blood cells and/or white blood cell subtypes from non-invasive capillary videos accurately, efficiently, and quantitatively determines white blood cell differential measurements and/or partial white blood cell differential measurements to assist medical personnel in treating various diseases and conditions associated with dangerously low levels of white blood cells, e.g., neutropenia, AIDs, autoimmune diseases, organ transplantation, patients treated with immunosuppressant drugs for various conditions, and the like. Once the machine learning subsystem efficiently and effectively learns and determines the presence of white blood cells and/or the subtype of white blood cells present in one or more optical absorption gaps using the annotated information from the second plurality of images acquired with the advanced optical device, the claimed method can then utilize a simple, portable and cost-effective imaging device, e.g., a capillaroscope to determine the presence of white bloods in OAGs and the subtype of the white blood cells and does not need to further utilize the advanced and expensive optical imaging system, e.g., SECM, SCAP, SCOPI, OPBM, and the like.

Using similar techniques as discussed above with reference to one or more of FIGS. 1-9, the method to determine density of red blood cells from non-invasive capillary videos of one embodiment of this invention includes acquiring a first plurality of images of a region of interest including one or more capillaries of a predetermined area of a human subject from non-invasive capillary videos captured with an optical device, step 200, FIG. 10. The first plurality of images is processed to determine one or more areas of hemoglobin optical absorption located in the capillary, step 202. The first plurality of images is annotated with an indication of any areas of hemoglobin optical absorption detected in the first plurality of images, step 204. A second plurality of images of the same region of interest of the same capillary is acquired with an advanced optical device capable of resolving cellular structure of red blood cells, step 206. The second plurality of images with an indication of a density of any red blood cell detected is spatiotemporally annotated in the second plurality of images, step 208. The first plurality of images and annotated information from the first plurality of images and annotated information from the spatiotemporally annotated second plurality of images are input into a machine learning subsystem configured to determine the density of any red blood cells present in the one or more optical absorption gaps in the first plurality of images, step 210.

In one example, red blood cell count may be determined from the density of red blood cells.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

What is claimed is:

1. A method to detect white blood cells and/or white blood cell subtypes from non-invasive capillary videos, the method comprising:
    acquiring a first plurality of images of a region of interest including one or more capillaries of a predetermined area of a human subject from non-invasive capillary videos captured with an optical device;
    processing the first plurality of images to determine one or more optical absorption gaps located in said capillary;
    annotating the first plurality of images with an indication of any optical absorption gap detected in the first plurality of images;
    acquiring a second plurality of images of the same region of interest of the same capillary with an advanced optical device capable of resolving cellular structure of white blood cells and white blood cell subtypes;
    spatiotemporally annotating the second plurality of images with an indication of any white blood cell detected and/or a subtype of any white blood cell detected in the second plurality of images; and
    inputting the first plurality of images and annotated information from the first plurality of images and annotated information from the spatiotemporally annotated second plurality of images into a machine learning subsystem configured to determine a presence of white blood cells and/or the subtype of any white blood cells present in the one or more optical absorption gaps.

2. The method of claim 1 in which the machine learning subsystem is further configured to determine a white blood cell subtype for any optical absorption gap detected in the first plurality of images.

3. The method of claim 2 in which the machine learning subsystem is further configured to determine full white blood cell differential measurements and/or partial white blood cell differential measurements.

4. The method of claim 1 further including temporally aligning the first plurality of images to the spatiotemporally annotated second plurality of images.

5. The method of claim 4 in which the temporally aligning includes creating said region of interest and said same region of interest by using a same objective lens on the optical device and the advanced optical device.

6. The method of claim 4 in which the temporally aligning includes creating said region of interest and said same region of interest by focusing the optical device and the advanced optical device at a same location in the capillary.

7. The method of claim 4 further including generating optical absorption gap reference data including a frame identifier and indication of any optical absorption gap detected in the first plurality of images.

8. The method of claim 7 further including generating spatiotemporally annotated lookup data including a frame identifier and indication of the subtype of any white blood cell present.

9. The method of claim 8 in which the temporally aligning the first plurality of images to the spatiotemporally annotated second plurality of images includes temporally aligning the frame identifier of the first plurality of images to the frame identifier of the visually spatiotemporally annotated second plurality of images.

10. The method of claim 9 further including inputting the first plurality of images, the optical absorption gap reference data, and the spatiotemporally annotated lookup data into the machine learning subsystem, the machine learning subsystem configured to output results data of the any white blood cells detected and/or the subtype of any white blood cells detected and compare the results table to ground truth data.

11. The method of claim 9 in which machine learning subsystem is configured to output results data of the any white blood cells detected and/or a subtype of any white blood cells detected for each optical absorption gap in the first plurality images and compare the results data to a ground truth data.

12. The method of claim 1 in which said spatiotemporally annotating the second plurality of images further includes indicating one or more of: a size, a granularity, a brightness, a speed, an elongation, and/or a margination of the white blood cells and/or a change of density of red blood cells located upstream or downstream from a location of white blood cells detected.

13. The method of claim 1 in which the subtype of the white blood cell includes a granulocyte, a neutrophil, a lymphocyte, a monocyte, an eosinophil or a basophil.

14. The method of claim 1 in which the optical device includes a high-resolution camera.

15. The method of claim 1 in which the advanced imaging device includes one or more of: a spectrally-encoded confocal microscopy (SECM) device, a swept confocally-aligned planar excitation (SCAPE) microscopy device, a scattering confocally aligned oblique plane imaging (SCOPI) device, or oblique back-illumination microscopy (OBM) device.

16. The method of claim 1 in which the predetermined area of the human subject includes one or more of: a finger, a nailfold, a toe, a tongue, a gum, a lip, a retina, and/or an earlobe.

17. The method of claim 1 in which the optical device is configured to output at least one optical absorption gap signal.

18. The method of claim 1 in which the advanced optical device is configured to output an advanced optical signal.

19. The method of claim 1 in which the spatiotemporally annotating the second plurality of images is performed by a human.

20. The method of claim 1 in which the spatiotemporally annotating the second plurality of images is performed by a processing subsystem.

21. The method of claim 1 further including determining the presence of white blood cells and/or the subtype of any white blood cells present in the one or more optical absorption gaps using the first plurality of images and annotated information from the first plurality of images and information from the machine learning subsystem which has learned and determined the presence of white blood cells and/or the subtype of white blood cells present in one or more optical absorption gaps using the annotated information from the second plurality of images acquired with the advanced optical device.

22. A method to detect white blood cells and/or white blood cell subtypes from non-invasive capillary videos, the method comprising:
   acquiring a first plurality of images of a region of interest including one or more capillaries of a predetermined area of a human subject from non-invasive capillary videos captured with an optical device;
   processing the first plurality of images to determine one or more optical absorption gaps located in said capillary;
   annotating the first plurality of images with an indication of any optical absorption gap detected in the first plurality of images; and
   determining a presence of white blood cells and/or the subtype of any white blood cells present in the one or more optical absorption gaps using the first plurality of images and annotated information from the first plurality of images and information from a machine learning subsystem which has learned and determined the presence of white blood cells and/or the subtype of white blood cells present in one or more optical absorption gaps using annotated information from a second plurality of images acquired with an advanced optical device.

23. A method to determine a density of red blood cells from non-invasive capillary videos, the method comprising:
   acquiring a first plurality of images of a region of interest including one or more capillaries of a predetermined area of a human subject from non-invasive capillary videos captured with an optical device;
   processing the first plurality of images to determine one or more area of hemoglobin optical absorption gaps located in said capillary;
   annotating the first plurality of images with an indication of any area of hemoglobin optical absorption gaps detected in the first plurality of images;
   acquiring a second plurality of images of the same region of interest of the same capillary with an advanced optical device capable of resolving cellular structure of red blood cells;
   spatiotemporally annotating the second plurality of images with an indication of a density of any red blood cells detected in the second plural of images; and
   inputting the first plurality of images and annotated information from the first plurality of images and annotated information from the spatiotemporally annotated second plurality of images into a machine learning subsystem configured to determine the density of any red blood cell cells present in the one or more optical absorption gaps.

24. The method of claim 23 in which a red blood cell count is determined from the density of red blood cells.

* * * * *